United States Patent [19]

Desgranchamps

[11] Patent Number: 4,808,341

[45] Date of Patent: Feb. 28, 1989

[54] PROCESS FOR THE SEPARATION OF MERCAPTANS CONTAINED IN GAS

[75] Inventor: Guy Desgranchamps, Lons, France

[73] Assignee: Societe Nationale Elf Aquitaine (Production), Courbevoie, France

[21] Appl. No.: 557,112

[22] Filed: Dec. 1, 1983

[30] Foreign Application Priority Data

Dec. 2, 1982 [FR] France .................................. 82 20178

[51] Int. Cl.$^4$ ............................................ C07C 139/00
[52] U.S. Cl. .............................. 260/504 R; 260/513 R
[58] Field of Search ........................... 260/513 R, 504 R

[56] References Cited

U.S. PATENT DOCUMENTS 4,239,696 12/1980 Schreyer .......................... 260/513 R

OTHER PUBLICATIONS

Gilbert Sulfonation & Related React. (1965), pp. 220, 221.

Chem Abst, Deschamps, vol. 71, (1969), 72672j.

*Primary Examiner*—Alan Siegel
*Attorney, Agent, or Firm*—Burgess, Ryan & Wayne

[57] ABSTRACT

A process for the separation of mercaptans from gases, and especially from natural gas by absorption in a hydrocarbon oil and regeneration of the oil by oxidation of the mercaptans to sulfonic acids. The oxidation can be carried out at the absorption temperature and pressure by means of an oxidant in an aqueous medium. The regenerated oil is recycled after separation from the aqueous phase containing the sulfonic acids.

33 Claims, No Drawings

PROCESS FOR THE SEPARATION OF MERCAPTANS CONTAINED IN GAS

FIELD OF THE INVENTION

The present invention is a process for the separation of mercaptans from gas compositions and particularly from natural gas.

BACKGROUND OF THE INVENTION

Sulfur containing gases, in general, contain sulfur in the form of hydrogen sulfide contaminated by variable quantities of mercaptans. These gases are generally treated in desulfurization units that operate either with "physical solvents" or with "chemical solvents". The "physical solvents" which are used in processes such as the SELEXOL, RECTISOL, PURISOL and SULFINOL processes absorb both hydrogen sulfide and mercaptans and desulfurization of the gas is complete in one zone.

In units that operate with "chemical solvents" such as monoethanolamine, diethanolamine or methyldiethanolamine, salts are only formed with the acid components of the gas, i.e, the hydrogen sulfide and the carbon dioxide, while essentially all of the mercaptans remain in the treated gas.

If the gas containing the mercaptans also contains higher hydrocarbons, the recovery of which is economically justified, the gas is subjected to an oil stripping treatment. This treatment comprises washing the gas with an oil at very low temperature (lower or equal to about $-30°$ C.). The oil simultaneously absorbs the mercaptans and the higher hydrocarbons. The mercaptans and higher hydrocarbons are separated from the absorption oil and removed. The mercaptans are generally recovered in the hydrocarbon fraction having a boiling point corresponding to the boiling point of the mercaptans.

In gases for commercial use, the total quantity of sulfur must be lower than 50 mg/m$^3$, and for the gases to be used in reforming units, the specifications are even more strict. For the majority of sulfur containing gases treated in desulfurization units using "chemical solvents" (amines), which are not subsequently submitted to an oil stripping treatment, a supplementary purification is necessary.

SUMMARY OF THE PRIOR ART

One process for the supplementary purification is the UOP, MEROX process. In this process, the gas to be purified is countercurrently contacted with an aqueous soda solution containing the MEROX catalyst. The extracted mercaptans are oxidized by oxygen to form disulfides. The source of the oxygen is generally air; the disulfides which are insoluble in the aqueous soda solution are separated by decantation.

The extraction of methyl mercaptan by an aqueous soda solution is easy; extraction is however more and more difficult for the homologs of higher molecular weight.

In addition, due to the usual presence of carbon dioxide in the gas to be treated, there is an irreversible consumption of the soda.

SUMMARY OF THE INVENTION

The present invention overcomes the deficiencies in prior art processes and removes all types of mercaptans contained in the gases which are treated.

The invention is a process for the removal of mercaptans contained in gases by absorption in a hydrocarbon oil and regeneration of the hydrocarbon oil by oxidizing the mercaptans contained in the oil to form sulfonic acids. The oxidation is carried out at a temperature and pressure in the range of the absorption by means of contact and reaction with an oxidizing agent, in an aqueous medium. The regenerated oil is recycled to the absorption zone after separation of the aqueous phase containing the sulfonic acids.

DETAILED DESCRIPTION OF THE INVENTION

The gases containing mercaptans can be contacted by a hydrocarbon oil preferably countercurrently in an absorption column or other type of gas-liquid contacting means. The gas is contacted with the hydrocarbon oil at the pressure of the gas being in general between about 3 and 15 MPa and preferably between about 5 and 10 MPa, the temperature varying between ambient temperature and about 60° C.

Under the absorption conditions, the oil absorbs the mercaptans and a certain amount of the hydrocarbons contained in the gas. The amount of the hydrocarbon absorbed is a Henry's Law function of the partial pressure of each of the hydrocarbons.

In classic gasoline recovery, the regeneration of the hydrocarbon absorption oil and the recovery of the hydrocarbons is carried out by fractional expansion. The mercaptans are generally present in the hydrocarbon fraction of corresponding boiling point; for example, methylmercaptan is present in the propane fraction.

Regeneration according to the invention selectively eliminates the mercaptans. The regeneration can take place at the same temperature and at the same pressure as the absorption. The recycled oil remains permanently charged with absorbed hydrocarbons in the proportions that correspond to the gas-liquid equilibrium at the temperature and pressure conditions of the absorber.

Regeneration of the hydrocarbon oil is carried out by a chemical process comprising oxidation of the mercaptans to sulfonic acids. The sulfonic acids are soluble in the aqueous phase that contains the oxidant, and are insoluble in the absorption oil.

The oxidation can be carried out by simultaneous introduction and contact of the mercaptan containing hydrocarbon absorption oil, to be regenerated and the oxidant, in an aqueous medium in a reactor. The reactor is preferably a countercurrent contacting means. The reactor should ensure good contact between the two phases. A plate or packed column is peferred as, for example, a column packed with Raschig rings. It is also possible to use a bubble cap column.

The reaction mixture withdrawn from the reactor is sent into a decanter.

The hydrocarbon loaded oil phase, from which the mercaptans have been reacted is recycled to the absorber. The aqueous phase containing the sulfonic acids, is separated from the oil. Where the oxidizing agent has been present in excess with respect to the mercaptans, the excess oxidizing agent is present in aqueous phase and it is advantageous to recycle the aqueous phase to the reactor. Make up oxidizing agent can be added to the recycle stream.

The operations can be conducted either continuously or batchwise.

Any water soluble oxidant able to oxidize the mercaptan to form sulfonic acids is suitable to carry out the process according to the invention; particularly useful are hydrogen peroxide, for example 30% volume hydrogen peroxide, or peracids. Peracids such as performic or peracetic acid are particularly useful.

According to a preferred embodiment of the invention, the oxidizing agent comprises a peracid formed in situ from the reaction of a carboxylic acid and hydrogen peroxide.

Any concentration of hydrogen peroxide can be used. However, for safety reasons, the operation should be limited to the use of solutions of about 50% volume. Solutions of about 30% volume hydrogen peroxide are preferred.

The carboxylic acids useful in the practice of the present invention have the general formula R—COOH; where R is an alkyl, halogeno-alkyl or aryl radical. The number of carbon atoms in the R group is not critical as long as the peracid formed from the acis is soluble in the aqueous solution.

Readily water-soluble acids are preferred, such as those for which R=H, $CH_3$, $CF_3$ and the like. Formic acid provides the highest reaction rates. The acid can be used at a ratio of about 0.1 to 1 moles per mole of hydrogen peroxide, preferably about 0.2 to 0.5 mole per mole $H_2O_2$.

Experience shows that the consumption of hydrogen peroxide is between about 3 and about 12 moles per mole of mercaptan. If the hydrogen peroxide is present in excess, the oxidation reaction of the mercaptans will reach total conversion after a certain time. The reaction rate is much higher when:

the $H_2O_2$/R SH ratio is higher
the amount of organic acid present is higher
the temperature is higher
the contact between the two phases is improved.

When excess quantities of hydrogen peroxide are introduced into the reactor, the excess hydrogen peroxide does not decompose but is present in the aqueous effluent from the reactor. The aqueous effluent can be recycled. There should be no hesitation in using excess hydrogen peroxide even in amounts as high as about 100 moles per mole of mercaptan, in order to profit from the higher reaction rates.

The recycling of aqueous effluents, after addition of make up hydrogen peroxide, also reduces the organic acid consumption.

Indeed, this acid in its peracid form acts as an active oxygen vector, but is recovered at the end of the process. It is thus sufficient to add, during continuous operation, quantities of organic acid corresponding to those eliminated in the purge flow of the aqueous phase loaded with sulfonic acids (these sulfonic acids furthermore facilitate oxidation of the mercaptans by contributing to catalysis of this reaction).

The oil used for the absorpti-on of the mercaptans should be readily available, sufficiently fluid at operating temperature and have a low volatility at the temperature and pressure of the process to minimize losses through vaporization into the gas stream.

Oils such as spindle oil, 100 NS oil or any other refining cut with equivalent properties is preferably used.

It is not possible to generalize the composition of the oil that circulates in the system since it is permanently loaded with hydrocarbons that are absorbed from the gas to be treated, in proportions which correspond to the gas-liquid equilibrium between the oil and the gas under the temperature and pressure conditions at which the absorber operates. The composition of the oil is therefore a function of the composition of the treated gas.

As indicated hereinabove, the absorption and regeneration steps, according to the present invention can be carried out at substantially the same pressure and the same temperature. The pressure is generally between about 5 and 10 MPa and the temperature between about 15 and 60° C.

EXAMPLE 2,000,000 standard cubic meters per day (S/m3/d) of a natural gas having the composition indicated hereinafter is treated in a conventional desulfurization unit making use of diethanolamine, under a pressure of 7 MPa:

|  | % by volume |
| --- | --- |
| $N_2$ | 1.4 |
| $CH_4$ | 71.1 |
| $C_2H_5$ | 2.5 |
| $C_3^+$ | traces |
| $H_2S$ | 15.1 |
| $CO_2$ | 9.9 |
| COS | 0.05 |
| RSH | 780 mg/m$^3$ expressed as sulfur |

At the exit of the primary desulfurization zone, the flow rate is 1,500,000 Sm$^3$/d gas at 50° C. and under 7 MPa, which gas has the following composition:

|  | ppm by volume |
| --- | --- |
| $CO_2$ | 1200 |
| $H_2S$ | 4 |
| $CH_3SH$ | 216 |
| $C_2H_5SH$ | 75 |
| $C_3H_7SH$ | 33 |
| $C_4H_9SH$ | 17 |

The gas is then countercurrently contacted by a flow-rate of 140 m$^3$/h spindle oil, having a specific gravity of 0.908, in an absorber comprising 24 perforated plates operating at 50° C. under 7 MPa.

The purified gas obtained at the exit of the absorber has the following composition:

|  | ppm by volume |
| --- | --- |
| $CO_2$ | 1200 |
| $H_2S$ | 3 |
| $CH_3SH$ | 20 |
| $C_2H_5SH$ | 5 |
| $C_3H_7SH$ | 2 |
| $C_4H_9SH$ | 1 |

The residual mercaptans correspond to the presence of 38 mg of sulfur/Sm$^3$. The elimination of mercaptans is 92%. The oil loaded with mercaptans drawn from the bottom of the absorber contains:

| mercaptans | ppm weight |
| --- | --- |
| $CH_3SH$ | 195 |

-continued

| mercaptans | ppm weight |
|---|---|
| $C_2H_5SH$ | 90 |
| $C_3H_7SH$ | 49 |
| $C_4H_9SH$ | 30 |

This loaded oil is introduced into the bottom of a column packed with Raschig rings; it is therein countercurrently contacted and treated by 6.8 m$^3$/h of an aqueous solution containing 8.74K moles of hydrogen peroxide and 3.97K moles of formic acid per m$^3$. The regeneration column operates at substantially the same pressure as the absorption column, i.e., at 7 MPa. It is maintained at 50° C. by immersed cooling means.

The aqueous solution was initially prepared by simultaneous injection into the storage tank, for the aqueous solution, 30% volume hydrogen peroxide and pure formic acid, in the volume ratio 6/1.

The organic phase comprises the continuous phase in the packed column. The working volume of the reactor provides a reaction time of 0.4 hours. The regenerated oil leaving the head of the reactor had a mercaptan analysis as follows:

| mercaptans | ppm weight |
|---|---|
| $CH_3SH$ | 10 |
| $C_2H_5SH$ | 6 |
| $C_3H_7SH$ | 8 |
| $C_4H_9SH$ | 6 |

The analysis indicates that on the average, 93% of the mercaptans initially present in the loaded oil, were reacted. The oil is recycled to the absorber to absorb additional mercaptans.

The aqueous phase drawn off at the bottom of the oil regeneration column is directed to a storage tank.

Analysis of the aqueous solution shows that its formic acid content has not changed; it contains, furthermore, sulfonic acids corresponding to the reacted mercaptans; it still contains 8.23K moles of hydrogen peroxide per cubic meter (m$^3$).

The hydrogen peroxide consumption is established at 4.5 moles per mole of reacted mercaptan.

The titre adjustment of the aqueous solution is achieved through the addition of 361 liters/h of 50% volume hydrogen peroxide to 6.44 cubic meters/hour (m$^3$/h) of aqueous solution drawn from the storage tank.

An equivalent flow rate of (361 l/h) purge is drawn off the storage tank.

To compensate for the loss of formic acid in the purge, it is necessary to add 54 l/h fresh make-up acid.

What is claimed is:

1. A process for the removal of mercaptans from a gas stream which comprises:
   (a) contacting the gas stream with a hydrocarbon absorption oil, in an absorption zone, to remove at least a portion of the mercaptans from the gas stream and form a hydrocarbon oil containing mercaptans;
   (b) contacting the hydrocarbon oil containing mercaptans with an aqueous solution of an oxidizing agent in a reaction zone to react at least a portion of the mercaptans, in the hydrocarbon oil containing mercaptans, to sulfonic acid and form an aqueous solution containing sulfonic acid and a hydrocarbon absorption oil.

2. The process of claim 1 wherein the aqueous solution containing sulfonic acid is separated from the hydrocarbon absorption oil and the hydrocarbon absorption oil is recycled to the absorption zone.

3. The process of claim 1 wherein the aqueous solution containing sulfonic acid is separated from the hydrocarbon absorption oil and the aqueous solution containing sulfonic acid is recycled to the reaction zone.

4. The process of claim 1 wherein the oxidizing agent is selected from the group consisting of hydrogen peroxide, a peracid and mixtures thereof.

5. The process of claim 2 wherein the oxidizing agent is selected from the group consisting of hydrogen peroxide, a peracid and mixtures thereof.

6. The process of claim 3 wherein the oxidizing agent is selected from the group consisting of hydrogen peroxide, a peracid and mixtures thereof.

7. The process of claim 4 wherein the oxidizing agent is hydrogen peroxide.

8. The process of claim 5 wherein the oxidizing agent is hydrogen peroxide.

9. The process of claim 6 wherein the oxidizing agent is hydrogen peroxide.

10. The process of claim 4 wherein the oxidizing agent is selected from the group consisting of a peracid and a mixture of peracid and hydrogen peroxide.

11. The process of claim 5 wherein the oxidizing agent is selected from the group consisting of a peracid and a mixture of peracid and hydrogen peroxide.

12. The process of claim 6 wherein the oxidizing agent is selected from the group consisting of a peracid and a mixture of peracid and hydrogen peroxide.

13. The process of claim 10 wherein the peracid comprises performic acid.

14. The process of claim 11 wherein the peracid comprises performic acid.

15. The process of claim 12 wherein the peracid comprises performic acid.

16. The process of claim 10 wherein the peracid or mixture of peracid and hydrogen peroxide is formed in situ by the reaction of a carboxylic acid and hydrogen peroxide.

17. The process of claim 11 wherein the peracid or mixture of peracid and hydrogen peroxide is formed in situ by the reaction of a carboxylic acid and hydrogen peroxide.

18. The process of claim 12 wherein the peracid or mixture of peracid and hydrogen peroxide is formed in situ by the reaction of a carboxylic acid and hydrogen peroxide.

19. The process of claim 16 wherein the molar ratio of carboxylic acid:hydrogen peroxide is from about 0.1:1 to 1:1.

20. The process of claim 17 wherein the molar ratio of carboxylic acid:hydrogen peroxide is from about 0.1:1 to 1:1.

21. The process of claim 18 wherein the molar ratio of carboxylic acid:hydrogen peroxide is from about 0.1:1 to 1:1.

22. The process of claim 19 wherein the amount of oxidizing agent in the aqueous solution is from about 3 to 100 moles per mole of mercaptan in the hydrocarbon oil containing mercaptan.

23. The process of claim 20 wherein the amount of oxidizing agent in the aqueous solution is from about 3 to 100 moles per mole of mercaptan in the hydrocarbon oil containing mercaptan.

24. The process of claim 21 wherein the amount of oxidizing agent in the aqueous solution is from about 3 to 100 moles per mole of mercaptan in the hydrocarbon oil containing mercaptan.

25. The process of claim 3 wherein the amount of oxidizing agent in the aqueous solution containing sulfonic acid is increased before the aqueous solution is recycled to the reaction zone.

26. The process of claim 6 wherein the amount of oxidizing agent in the aqueous solution containing sulfonic acid is increased before the aqueous solution is recycled to the reaction zone.

27. The process of claim 12 wherein the amount of oxidizing agent in the aqueous solution containing sulfonic acid is increased before the aqueous solution is recycled to the reaction zone.

28. The process of claim 1 wherein the temperature is between about 20° C. and 60° C.

29. The process of claim 2 wherein the temperature is between about 20° C. and 60° C.

30. The process of claim 3 wherein the temperature is between about 20° C. and 60° C.

31. The process of claim 28 wherein the pressure is between about 5 and 10 MPa.

32. The process of claim 29 wherein the pressure is between about 5 and 10 MPa.

33. The process of claim 30 wherein the pressure is between about 5 and 10 MPa.

* * * * *